(12) United States Patent
Galavotti et al.

(10) Patent No.: US 9,308,314 B2
(45) Date of Patent: Apr. 12, 2016

(54) DISPOSABLE DEVICE FOR CENTRIFUGAL BLOOD SEPARATION

(75) Inventors: Andrea Galavotti, Mirandola (IT); Elisa Maculan, Mirandola (IT); Gianpaolo Simonini, Reggio Emilia (IT)

(73) Assignee: Sorin Group Italia S.r.l., Milan (IT)

( * ) Notice: Subject to any disclaimer, the term of this patent is extended or adjusted under 35 U.S.C. 154(b) by 168 days.

(21) Appl. No.: 14/110,435

(22) PCT Filed: Mar. 13, 2012

(86) PCT No.: PCT/IB2012/051177
§ 371 (c)(1),
(2), (4) Date: Oct. 28, 2013

(87) PCT Pub. No.: WO2012/137086
PCT Pub. Date: Oct. 11, 2012

(65) Prior Publication Data
US 2014/0045672 A1     Feb. 13, 2014

(30) Foreign Application Priority Data

Apr. 8, 2011   (IT) .............................. TO2011A0321

(51) Int. Cl.
| | |
|---|---|
| *A61M 1/36* | (2006.01) |
| *B04B 5/04* | (2006.01) |
| *B04B 7/08* | (2006.01) |
| *B04B 11/06* | (2006.01) |

(52) U.S. Cl.
CPC ............ *A61M 1/3693* (2013.01); *B04B 5/0442* (2013.01); *B04B 7/08* (2013.01); *B04B 11/06* (2013.01); *B04B 2005/0464* (2013.01)

(58) Field of Classification Search
CPC ........ B04B 5/0442; B04B 7/08; B04B 11/06; B04B 2005/0464; A61M 1/3693
USPC ................................................ 494/44, 23, 27
See application file for complete search history.

(56) References Cited

U.S. PATENT DOCUMENTS

| | | |
|---|---|---|
| 1,385,306 A | 7/1921 | Clayton |
| 2,835,517 A | 5/1958 | Beerli |
| 3,317,127 A | 5/1967 | Cole |
| 3,409,213 A | 11/1968 | Latham, Jr. |

(Continued)

FOREIGN PATENT DOCUMENTS

| | | |
|---|---|---|
| EP | 0682953 A1 | 11/1995 |
| EP | 0931554 A2 | 7/1999 |

(Continued)

OTHER PUBLICATIONS

European Search Report issued in EP Application No. 06124795, mailed May 11, 2007, 8 pages.

(Continued)

*Primary Examiner* — Charles Cooley
*Assistant Examiner* — Shuyi S Liu
(74) *Attorney, Agent, or Firm* — Faegre Baker Daniels LLP

(57) ABSTRACT

A continuous centrifugal blood separation device has a simple and reliable structure. The continuous blood centrifugal device includes an RBC (red blood cell) collector that is coaxial with a supernatant collector. The continuous blood centrifugal device includes an axial symmetric barrier disposed between the RBC collector and the supernatant collector in order to avoid turbulence that can otherwise be caused by the supernatant collector.

13 Claims, 4 Drawing Sheets

(56) References Cited

U.S. PATENT DOCUMENTS

| | | |
|---|---|---|
| 3,519,201 A | 7/1970 | Robert et al. |
| 3,565,330 A | 2/1971 | Latham, Jr. |
| 3,581,981 A | 6/1971 | Latham, Jr. |
| 3,785,549 A | 1/1974 | Latham, Jr. |
| 4,140,268 A | 2/1979 | Lacour |
| 4,668,214 A | 5/1987 | Reeder |
| 4,718,888 A | 1/1988 | Darnell |
| 4,795,419 A | 1/1989 | Yawn et al. |
| 4,838,849 A | 6/1989 | Calari |
| 4,889,524 A | 12/1989 | Fell et al. |
| 4,919,817 A | 4/1990 | Schoendorfer et al. |
| 5,060,957 A | 10/1991 | Stolzenberg et al. |
| 5,062,826 A | 11/1991 | Mantovani et al. |
| 5,104,372 A | 4/1992 | Rossetto |
| 5,288,088 A | 2/1994 | Santandrea et al. |
| 5,298,171 A | 3/1994 | Biesel |
| 5,311,908 A | 5/1994 | Barone et al. |
| 5,312,319 A | 5/1994 | Salter |
| 5,379,775 A | 1/1995 | Kruse |
| 5,383,911 A | 1/1995 | Mann |
| 5,385,539 A | 1/1995 | Maynard |
| 5,387,174 A | 2/1995 | Rochat |
| 5,417,715 A | 5/1995 | Noren et al. |
| 5,423,738 A | 6/1995 | Robinson et al. |
| 5,478,479 A | 12/1995 | Herrig |
| 5,505,683 A | 4/1996 | Geringer et al. |
| 5,514,070 A * | 5/1996 | Pages .............................. 494/41 |
| 5,591,113 A | 1/1997 | Darnell et al. |
| 5,607,579 A | 3/1997 | Latham, Jr. et al. |
| 5,658,231 A | 8/1997 | Schmitt et al. |
| 5,730,883 A | 3/1998 | Brown |
| 5,851,169 A | 12/1998 | Meresz et al. |
| 5,873,810 A | 2/1999 | Holm et al. |
| 5,876,611 A | 3/1999 | Shettigar |
| 5,919,125 A | 7/1999 | Berch |
| 5,964,690 A | 10/1999 | Wright et al. |
| 6,241,649 B1 | 6/2001 | Zanella et al. |
| 6,299,784 B1 | 10/2001 | Biesel |
| 6,348,031 B1 | 2/2002 | Unger et al. |
| 6,352,499 B1 | 3/2002 | Geigle |
| 6,416,456 B2 | 7/2002 | Zanella et al. |
| 6,605,028 B2 | 8/2003 | Dolecek |
| 6,629,919 B2 | 10/2003 | Egozy et al. |
| 6,716,151 B2 | 4/2004 | Panzani et al. |
| 7,001,323 B2 | 2/2006 | Panzani et al. |
| 7,211,037 B2 | 5/2007 | Briggs et |
| 7,452,322 B2 | 11/2008 | Headley et al. |
| 7,993,257 B2 | 8/2011 | Simonini et al. |
| 8,262,552 B2 | 9/2012 | Simonini et al. |
| 2003/0181305 A1 | 9/2003 | Briggs et al. |
| 2005/0054508 A1 | 3/2005 | Panzani et al. |
| 2006/0040818 A1 | 2/2006 | Jorgensen et al. |
| 2007/0213191 A1 | 9/2007 | Chammas |
| 2008/0124700 A1 | 5/2008 | Fortini et al. |
| 2008/0128367 A1 | 6/2008 | Rochat |
| 2008/0132397 A1 | 6/2008 | Rochat |
| 2008/0153686 A1 | 6/2008 | Rochat |
| 2008/0264841 A1 | 10/2008 | Rochat |
| 2009/0050579 A1 | 2/2009 | Rochat et al. |
| 2009/0065424 A1 * | 3/2009 | Rochat ........................ 210/380.3 |
| 2009/0305863 A1 | 12/2009 | Simonini et al. |
| 2011/0237418 A1 | 9/2011 | Chammas |
| 2011/0256999 A1 | 10/2011 | Simonini et al. |
| 2013/0079211 A1 | 3/2013 | Simonini et al. |
| 2013/0331815 A1 | 12/2013 | Fortini et al. |

FOREIGN PATENT DOCUMENTS

| | | |
|---|---|---|
| EP | 1254675 A1 | 11/2002 |
| EP | 1512419 B1 | 3/2005 |
| EP | 2138237 B1 | 12/2009 |
| JP | 09164343 A | 6/1997 |
| JP | 9192215 A | 7/1997 |
| JP | 2005081087 A | 3/2005 |
| JP | 2009291335 A | 12/2009 |
| JP | 2010042398 A | 2/2010 |
| WO | WO 8001470 A1 * | 7/1980 .......... A61M 1/3693 |
| WO | WO9829149 A1 | 7/1998 |
| WO | WO2007095771 A1 | 8/2007 |
| WO | WO2007098623 A1 | 9/2007 |

OTHER PUBLICATIONS

Gilbert et al., "Hematocrit Monitor", Critical Care Medicine, 17(9):929-933 (Sep. 1989).

International Search Report and Written Opinion issued in PCT/IB2012/051177, mailed Jul. 19, 2012, 11 pages.

International Search Report for European Application No. 08157932, mailed Nov. 19, 2008, 4 pages.

Steinke et al., "Role of Light Scattering in Whole Blood Oximetry", IEEE Transactions on Biomedical Engineering, BME-33(3):294-301 (Mar. 1986).

Zdrojkowski et al., "Optical Transmission and Reflection by Blood", IEEE Transactions on Biomedical Engineering, BME-17(2):122-128 (Apr. 1970).

* cited by examiner

DISPOSABLE DEVICE FOR CENTRIFUGAL BLOOD SEPARATION

CROSS-REFERENCE TO RELATED APPLICATIONS

This application is a national phase application of PCT Application No. PCT/IB2012/051177, internationally filed Mar. 13, 2012, which claims priority to Italian Application No. TO2011A000321, filed Apr. 8, 2011, both of which are herein incorporated by reference in their entirety.

TECHNICAL FIELD

The disclosure pertains generally to devices for blood separation and more particularly to disposable devices for continuous blood separation.

BACKGROUND

A variety of devices for blood separation, including centrifugal devices, are known. Some blood separation devices are limited to a discontinuous process in which a bowl-shaped chamber is filled and then emptied. An example is the Latham bowl, which includes a cone shaped centrifuging chamber with inlet and outlet channels that are part of a stationary element coupled to the rotating chamber via a low friction rotary seal whose function, besides sealing, is to preserve blood sterility during operation. Once inside the device, blood, due to centrifugal force, separates into components in the space between the external and the internal bowl. The lighter component (the supernatant, i.e., plasma with various impurities coming from the surgical field, platelets and white cells, collects towards the inner side of the chamber while the heavier blood components, i.e. the red blood cells, accumulate and concentrate towards the bowl outer diameter. Once the bowl is almost completely filled with red cells, blood flow is stopped. Saline is forced through the red cells and washes them by removing the impurities. After a certain amount of saline has passed through the bowl, the washing step is finished and the centrifugation is stopped. The red cells are then removed from the bowl and made available for reinfusion to the patient. The bowl is now ready to start a new cycle.

An existing device that allows continuous flow separation of salvaged blood is the Fresenius C.A.T.S., but it uses a non-axial symmetric chamber, having the shape of a tubular channel with variable radius. The Fresenius C.A.T.S. is a rather complex unit that does not provide a performance that is superior to that provided by the Latham bowl.

Another continuous flow device, the Biofluid bowl, is described in WO 2007/098623. The Biofluid bowl is equipped with a red blood cell collector and a supernatant collector. Blood entering the bowl hits the bottom of the bowl and, due to centrifugation, is pushed out forming a thin layer on the inner surface of the bowl in which the blood separates into red blood cells on the outside of the thin layer and supernatant on the inside of the thin layer. As the two layers reach the red blood cell collector and the supernatant collector, each layer can be separately collected. A continuous saline flow injected into the bowl through an expressly provided inlet removes impurities from the red blood cell layer.

SUMMARY

The present invention relates to centrifugal separation of blood into components to be returned to a patient, such as red blood cells, and other components to be disposed of, such as supernatant. Example 1 is a disposable continuous blood centrifugal device that includes a rotatable housing and a rotatable inner bowl disposed within the rotatable housing and defining a space between the rotatable inner bowl and the rotatable housing that is sized to permit blood to separate into layers, with a more dense layer closest to the rotatable housing and a less dense layer closest to the rotatable inner bowl. The device includes a first collector configured to collect blood components from within the more dense layer and a second collector configured to collect blood components from within the less dense layer. A rotatable barrier is disposed within the rotatable housing above the rotatable inner bowl and is configured to direct blood components within the more dense layer towards the first collector and to direct blood components within the less dense layer towards the second collector. A stationary structure extends downwardly through the rotatable housing and the rotatable inner bowl, the stationary structure including a blood inlet, a first outlet in fluid communication with the first collector and a second outlet in fluid communication with the second collector.

In Example 2, the continuous blood centrifugal device of Example 1 in which a first collection chamber in which the first collector is disposed is formed between the rotatable barrier and a top of the rotatable housing.

In Example 3, the continuous blood centrifugal device of Example 1 or Example 2 in which a second collection chamber in which the second collector is disposed is formed within the rotatable barrier or between the rotatable barrier and the rotatable inner bowl.

In Example 4, the continuous blood centrifugal device of any of Examples 1-3 in which the blood inlet extends to a position near a bottom of the rotatable housing. In Example 5, the continuous blood centrifugal device of any of Examples 1-4 in which the stationary structure includes a saline inlet that extends to a position near the bottom of the rotatable housing.

In Example 6, the continuous blood centrifugal device of any of Examples 1-5 in which the rotatable housing has a frustoconical shape.

In Example 7, the continuous blood centrifugal device of Example 6 in which the rotatable inner bowl has a tapered outer surface.

In Example 8, the continuous blood centrifugal device of Example 7 in which the tapered outer surface is configured to provide a non-uniform size of the space defined between the inner rotatable bowl and the outer housing.

In Example 9, the continuous blood centrifugal device of any of Examples 1-5 in which the rotatable housing has a cylindrical shape.

In Example 10, the continuous blood centrifugal device of Example 9 in which the rotatable inner bowl includes a cylindrical outer surface.

In Example 11, the continuous blood centrifugal device of Example 10 in which the cylindrical outer surface is configured to provide a uniform annular shape of the space defined between the inner rotatable bowl and the outer housing.

In Example 12, the continuous blood centrifugal device of any of Examples 1-11 in which the rotatable barrier includes a disk portion that extends between the first collector and the second collector in order to reduce turbulence that could otherwise cause remixing of the blood components within the more dense layer with the blood components within the less dense layer.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
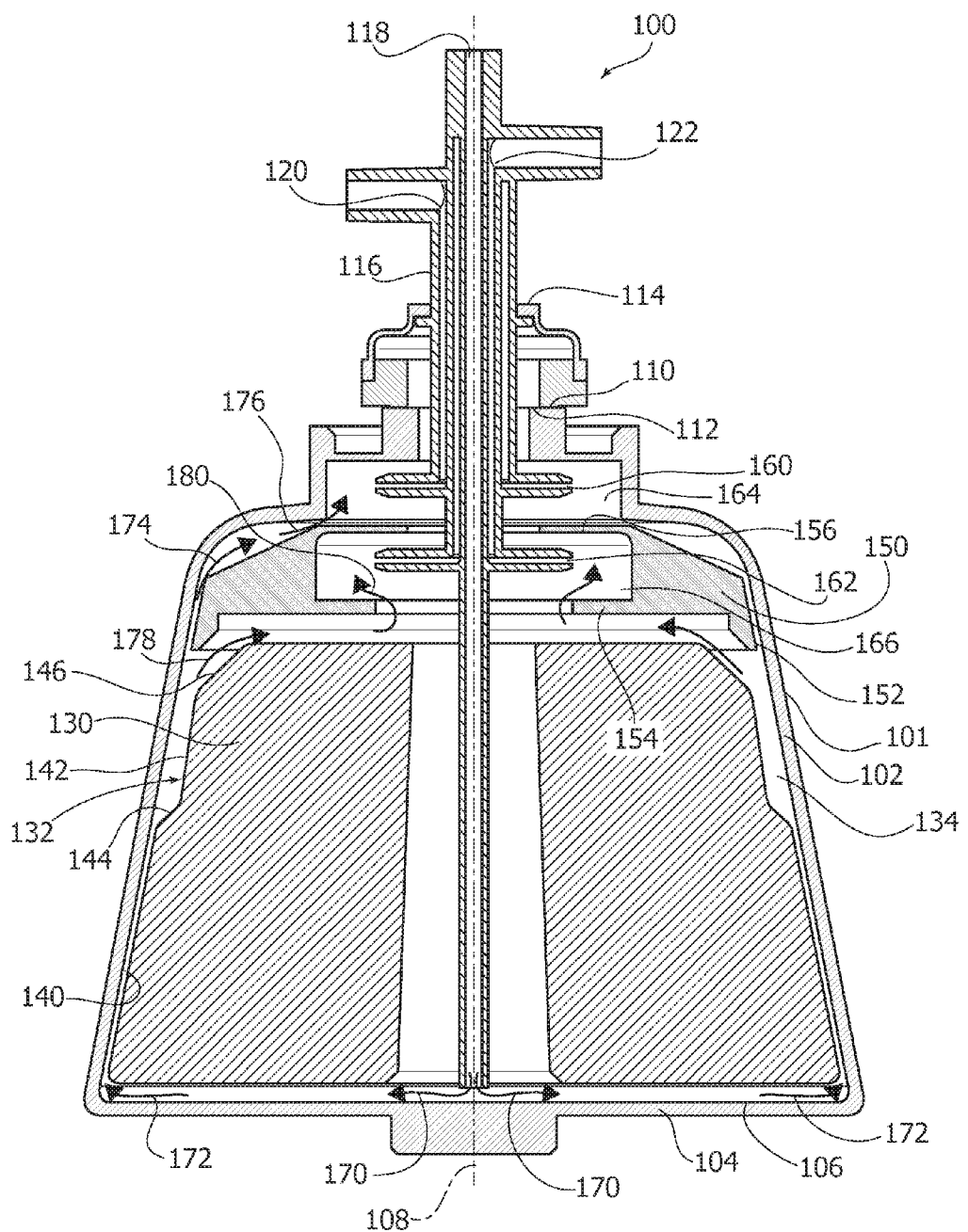
FIG. 1 is a schematic longitudinal section of the inventive continuous blood centrifugal device in accordance with an embodiment of the present invention.

The invention pertains to an inventive continuous centrifugal blood separation device that has a simple and reliable structure, like the Latham bowl, and avoids some functional difficulties observed with the Biofluid bowl. The inventive continuous blood centrifugal device, in comparison with the Latham bowl, includes an RBC (red blood cell) collector that is coaxial with a supernatant collector. The inventive continuous blood centrifugal device includes an axial symmetric barrier disposed between the RBC collector and the supernatant collector in order to avoid turbulence that can otherwise be caused by the supernatant collector.

In comparison to the Biofluid bowl, the inventive continuous blood centrifugal device adds an internal body or bowl. The internal bowl provides a number of advantages. For example, adding the internal bowl helps to improve the stability of the device. The internal bowl helps to avoid the loss of air that may otherwise cause the Biofluid bowl to fill with blood during use.

In some embodiments, the inventive continuous blood centrifugal device includes an internal body or bowl. In some embodiments, the blood centrifugal device can have a variety of different bowl shapes, such as either conical or cylindrical. The outer bowl may be cylindrical, conically tapered upwards, or even a downwards taper. In some embodiments, having a non-cylindrical shape improves saline RBC washing performance. In some embodiments, a tapered shape permits either a constant or non-constant, as desired, thickness of the blood layer within the outer bowl. In some embodiments, this may permit optimization of fluid dynamics and/or sedimentation speed.

In some embodiments, the inventive continuous blood centrifugal device permits use of a relatively wide bowl diameter, in comparison to the diameter of the RBC collector. This is an advantage not afforded by the Biofluid bowl, since in the Biofluid bowl the diameter of the RBC collector (relatively small) corresponds to the layer at which the RBC separation takes place. This prevents the use of wide bowl diameters, since a collector diameter increase means an increase of tangential speed and shear stresses (on equal terms of centrifugal acceleration).

In comparison, the inventive continuous blood centrifugal device provides for a wide diameter bowl with a small RBC collector diameter, allowing a separation device with relatively lower height, which can be more easily mounted on a centrifuge plate. Furthermore, the inventive continuous blood centrifugal device allows a wider distance between the turbulences induced by the supernatant collector and the separation line between RBCs and supernatant, thus improving separation stability.

In some embodiments, blood entering the inventive continuous blood centrifugal device is pushed by pump to the bottom of the chamber and, due to centrifugation, moves upwards in the space between the external bowl and the internal bowl. Blood separates into red cells (on the outside of this space) and supernatant (on the inside of this space). When these two layers reach the two extraction collectors, they can be separately collected outside of the centrifuge. The separation can continue as long as blood is introduced into the chamber with supernatant and RBC being separately collected in a continuous way. Washing can be achieved in two different ways: by means of blood predilution with saline; or by using a second inlet channel for saline, along which saline is pushed into the centrifuging chamber, near the bottom, so that it can pass through the RBC layer removing all the impurities and dragging them towards the supernatant collector.

Turning to the Figures, FIG. 1 is a schematic illustration of a continuous blood centrifugal device 100 in accordance with embodiments of the present invention. As illustrated in FIG. 1, the centrifugal device 100 includes a housing 101 including an inner surface 102 and a bottom 104. The bottom 104 includes an inner surface 106. The housing 101 rotates about an axis 108. The centrifugal device 100 includes an upper end 110 that has a circular opening 112 that is provided with a rotary joint 114 that forms a seal. The sealing rotary joint 114 is designed to ensure sterility inside the centrifugal device 100 and surrounds a stationary member 116 that extends into the housing 101 along the axis 108.

In some embodiments, as illustrated, the stationary member 116 includes several channels that provide an easy exchange of fluids into and out of the centrifugal device 100. In the illustrated embodiment, the stationary member 116 includes a blood supply channel 118 for supplying blood to the centrifugal device 100. In some embodiments, the blood supply channel 118 extends downwardly (in the illustrated orientation) to a point where the blood supply channel 118 nearly touches the inner surface 106 of the bottom 104. In some embodiments, the flow of blood entering the centrifugal device 100 is regulated in accordance with a measured hematocrit of the collected red blood cells in order to maintain a constant flow or supply of red blood cells. In some embodiments, a pump or valve (not illustrated) may be used to control the flow of blood supplied to the blood supply channel 118.

The stationary member 116 includes a first outlet channel 120 for extracting a first separated component, such as concentrated red blood cells, and a second outlet channel 122 for extracting a second separated component, such as supernatant. Illustrative but non-limiting examples of what may be separated as part of the supernatant includes plasma mixed with white blood cells, platelets, and added liquids such as saline, anticoagulant and other solutions.

In some embodiments, the centrifugal device 100 includes a rotatable inner bowl 130 having an outer surface 132. A space 134 is defined between the outer surface 132 of the rotatable inner bowl 130 and the inner surface 102 of the housing 101. This space 134 may be sized and/or otherwise configured to permit blood components to separate within the space according to their relative densities. In some embodiments, as the centrifugal device 100 rotates, relatively denser blood components such as red blood cells may migrate within the space 134 towards the inner surface 102 of the housing 101 while relatively less dense blood components such as the supernatant may migrate within the space 134 towards the outer surface 132 of the inner rotatable bowl 130.

In some embodiments, the space 134 may be configured to improve or optimize the density-based separation of the blood components. In some embodiments, the outer surface 132 of the rotatable inner bowl 130 may have a tapered shape that matches a profile of the housing 101. In some embodiments, as illustrated, the outer surface 132 of the rotatable inner bowl 130 may have a non-constant profile resulting in a non-constant size for the space 134. As illustrated, the outer surface 132 of the rotatable inner bowl 130 includes a first portion 140 that is substantially parallel to the inner surface 102 of the housing 101, a second portion 142 that is spaced further apart from the inner surface 102 yet still substantially parallel thereto, and an intervening transition portion 144. The outer surface 132 also includes an upper tapered portion 146.

In some embodiments, the centrifugal device 100 includes a barrier 150 that is disposed within the housing 101 and positioned above the rotatable inner bowl 130. The barrier 150 is concentric to the axis 108 and includes a periphery 152. A first collection chamber 164 is formed between the housing 101 and an upper disk portion 156 of the barrier 150. A second collection chamber 166 is formed between the upper disk portion 156 and a lower disk portion 154. In some embodiments, as illustrated, a first collector 160 that is in fluid communication with the first outlet channel 120 is disposed within the first collection chamber 164. In some embodiments, as illustrated, a second collector 162 that is in fluid communication with the second outlet channel 122 is disposed within the second collection chamber 166.

In use, blood enters the centrifugal device 100 through the supply channel 118. Blood passes down through the blood supply channel 118 and exits the blood supply channel 118 near the bottom 106 of the housing 101 as indicated by arrows 170. Blood passes into the space 134 as indicated by arrows 172. As blood travels upward through the space 134 as a result of centrifugal forces, the blood separates into a lighter layer relatively closer to the rotatable inner bowl 130 and a heavier layer that is relatively closer to the housing 101. The barrier 150 has an outer diameter, at least along a lower edge thereof, that spans beyond an interface (not visible) between the lighter layer (the supernatant) and the heavier layer (the red blood cells).

As a result, the relatively heavier (more dense) materials such as red blood cells follow a path indicated by arrows 174 and 176 and flow into the first collection chamber 164. From there, the red blood cells are withdrawn into the first collector 160 and flow up through the first outlet channel 120. The first outlet channel 120 may, in some embodiments, provide the red blood cells directly to a patient. In some embodiments, the red blood cells exiting the first outlet channel 120 may be held in a blood reservoir, blood bag, or the like, until the red blood cells are returned to the patient or otherwise used. The relatively lighter (less dense) materials follow a path indicated by arrows 178 and 180 and flow into the second collection chamber 166. From there, the less dense materials such as the supernatant are withdrawn into the second collector 162 and flow up through the second outlet channel 122.

The centrifugal device 100 may be formed of any suitable material. In some embodiments, the housing 101 is formed of a transparent polymer such as a polycarbonate so that the space 134 may be viewed. In some embodiments, the rotatable inner bowl 130 may be formed of any desired polymeric material such as polycarbonate. In some embodiments, the barrier 150 may be formed of any desired polymeric material such as polycarbonate.

Figure 2:
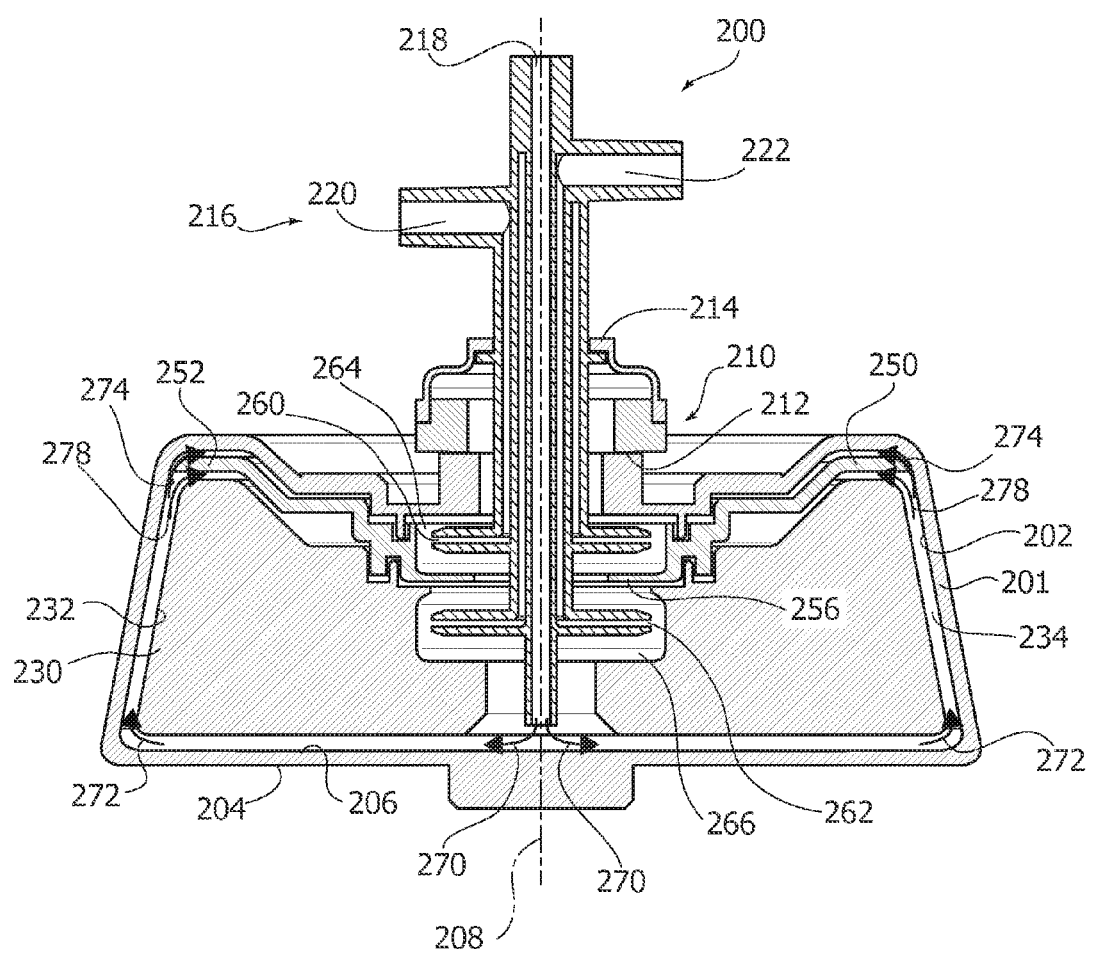
FIG. 2 is a schematic longitudinal section of the inventive continuous blood centrifugal device in accordance with an embodiment of the present invention.

FIG. 2 is a schematic illustration of a continuous blood centrifugal device 200 in accordance with embodiments of the present invention. As illustrated in FIG. 2, the centrifugal device 200 includes a housing 201 including an inner surface 202 and a bottom 204. The bottom 204 includes an inner surface 206. The housing 201 rotates about an axis 208. The centrifugal device 200 includes an upper end 210 that has a circular opening 212 that is provided with a rotary joint 214 that forms a seal. The sealing rotary joint 214 is designed to ensure sterility inside the centrifugal device 200 and surrounds a stationary member 216 that extends into the housing 201 along the axis 208.

In some embodiments, as illustrated, the stationary member 216 includes a blood supply channel 218 for supplying blood to the centrifugal device 200. In some embodiments, the blood supply channel 218 extends downwardly (in the illustrated orientation) to a point where the blood supply channel 218 nearly touches the inner surface 206 of the bottom 204. The stationary member 216 includes a first outlet channel 220 for extracting a first separated component, such as concentrated red blood cells, and a second outlet channel 222 for extracting a second separated component, such as supernatant.

In some embodiments, the centrifugal device 200 includes a rotatable inner bowl 230 having an outer surface 232. A space 234 is defined between the outer surface 232 of the rotatable inner bowl 230 and the inner surface 202 of the housing 201. This space 234 may be sized and/or otherwise configured to permit blood components to separate within the space according to their relative densities as the centrifugal device 200 rotates. In some embodiments, the space 234 may be configured to improve or optimize the density-based separation of the blood components. In some embodiments, the outer surface 232 of the rotatable inner bowl 230 may have a tapered shape that matches a profile of the housing 201.

In some embodiments, the centrifugal device 200 includes a barrier 250 that is disposed within the housing 201 and positioned above the rotatable inner bowl 230. The barrier 250 is concentric to the axis 208 and includes a periphery 252. A first collection chamber 264 is formed between the housing 201 and a disk portion 256 of the barrier 250. A second collection chamber 266 is formed between the disk portion 256 and the rotatable inner bowl 230. In some embodiments, as illustrated, a first collector 260 that is in fluid communication with the first outlet channel 220 is disposed within the first collection chamber 264. In some embodiments, as illustrated, a second collector 262 that is in fluid communication with the second outlet channel 222 is disposed within the second collection chamber 266.

In use, blood enters the centrifugal device 200 through the blood supply channel 218 and exits the blood supply channel 218 near the bottom 206 of the housing 201 as indicated by arrows 270. Blood passes into the space 234 as indicated by arrows 272. As blood travels upward through the space 234 as a result of centrifugal forces, the blood separates into a lighter layer relatively closer to the rotatable inner bowl 230 and a heavier layer that is relatively closer to the housing 201. The barrier 250 has an outer diameter, at least along a lower edge thereof, that spans beyond an interface (not visible) between the lighter layer (the supernatant) and the heavier layer (the red blood cells).

As a result, the relatively heavier (more dense) materials such as red blood cells follow a path indicated by arrows 274 and flow into the first collection chamber 264. From there, the red blood cells are withdrawn into the first collector 260 and flow up through the first outlet channel 220. The relatively lighter (less dense) materials follow a path indicated by arrows 278 and flow into the second collection chamber 266. From there, the less dense materials such as the supernatant are withdrawn into the second collector 262 and flow up through the second outlet channel 222.

Figure 3:
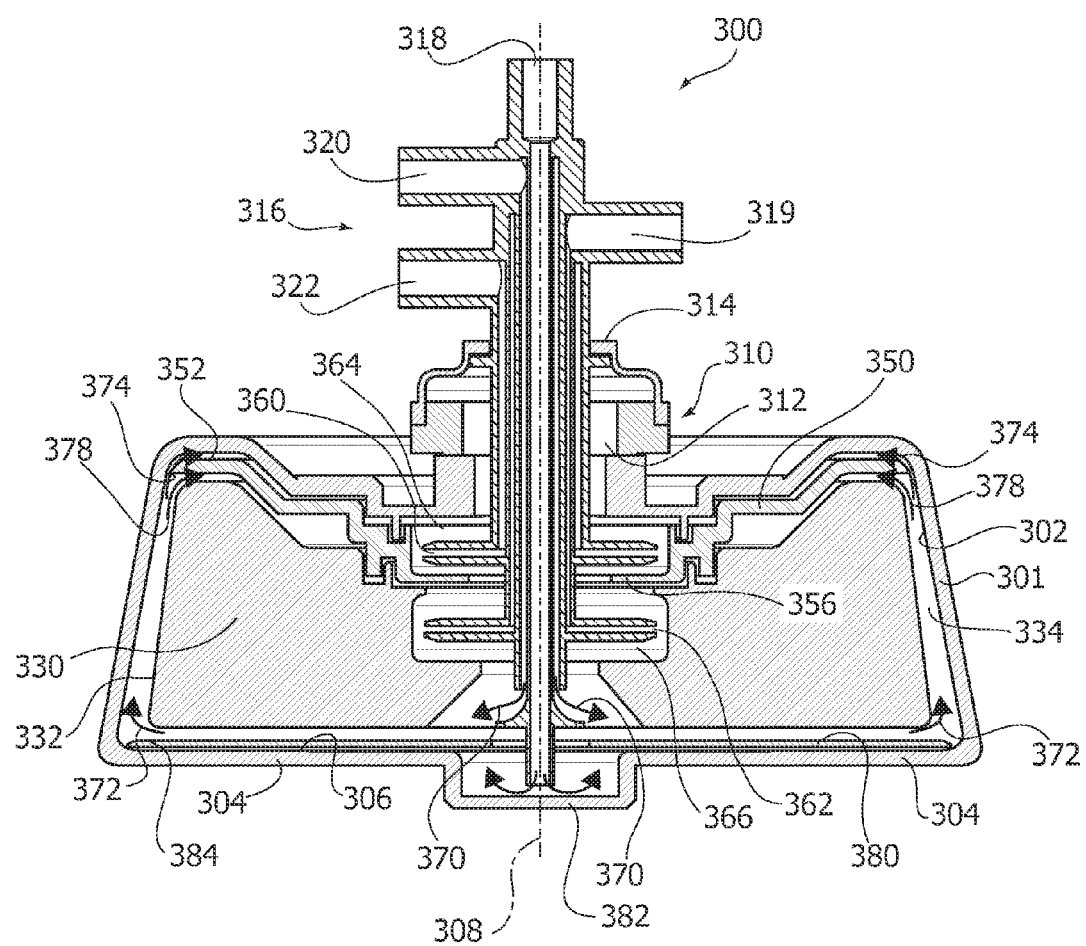
FIG. 3 is a schematic longitudinal section of the inventive continuous blood centrifugal device in accordance with an embodiment of the present invention.

FIG. 3 is a schematic illustration of a continuous blood centrifugal device 300 in accordance with embodiments of the present invention. As illustrated in FIG. 3, the centrifugal device 300 includes a housing 301 including an inner surface 302 and a bottom 304. The bottom 304 includes an inner surface 306. The housing 301 rotates about an axis 308. The centrifugal device 300 includes an upper end 310 that has a circular opening 312 that is provided with a rotary joint 314 that forms a seal. The sealing rotary joint 314 is designed to ensure sterility inside the centrifugal device 300 and surrounds a stationary member 316 that extends into the housing 301 along the axis 308.

In some embodiments, as illustrated, the stationary member 316 includes a blood supply channel 320 for supplying blood to the centrifugal device 300. In some embodiments, the blood supply channel 320 extends downwardly (in the illustrated orientation) to a point where the blood supply channel 320 nearly touches the deflector 380. In some embodiments, as illustrated, the stationary member 316 includes a saline supply channel 318 for providing saline for washing the red blood cells, as will be discussed. The stationary member 316 includes a first outlet channel 322 for extracting a first separated component, such as concentrated red blood cells, and a second outlet channel 319 for extracting a second separated component, such as supernatant.

In some embodiments, the centrifugal device 300 includes a rotatable inner bowl 330 having an outer surface 332. A space 334 is defined between the outer surface 332 of the rotatable inner bowl 330 and the inner surface 302 of the housing 301. This space 334 may be sized and/or otherwise configured to permit blood components to separate within the space according to their relative densities as the centrifugal device 300 rotates. In some embodiments, the space 334 may be configured to improve or optimize the density-based separation of the blood components. In some embodiments, the outer surface 332 of the rotatable inner bowl 330 may have a tapered shape that matches a profile of the housing 301. In some embodiments, as illustrated, the outer surface 332 of the rotatable inner bowl 330 may have a tapered profile that does not match a profile of the housing 301, thereby providing the space 334 with a non-constant size.

In some embodiments, the centrifugal device 300 includes a barrier 350 that is disposed within the housing 301 and positioned above the rotatable inner bowl 330. The barrier 350 is concentric to the axis 308 and includes a periphery 352. A first collection chamber 364 is formed between the housing 301 and a disk portion 356 of the barrier 350. A second collection chamber 366 is formed between the disk portion 356 and the rotatable inner bowl 330. In some embodiments, as illustrated, a first collector 360 that is in fluid communication with the first outlet channel 322 is disposed within the first collection chamber 364. In some embodiments, as illustrated, a second collector 362 that is in fluid communication with the second outlet channel 319 is disposed within the second collection chamber 366.

In use, blood enters the centrifugal device 300 through the blood supply channel 320 and exits the blood supply channel 320 near the deflector 380 as indicated by arrows 370. Blood passes into the space 334 as indicated by arrows 372. As blood travels upward through the space 334 as a result of centrifugal forces, the blood separates into a lighter layer relatively closer to the rotatable inner bowl 330 and a heavier layer that is relatively closer to the housing 301. The barrier 350 has an outer diameter, at least along a lower edge thereof, that spans beyond an interface (not visible) between the lighter layer (the supernatant) and the heavier layer (the red blood cells).

As a result, the relatively heavier (more dense) materials such as red blood cells follow a path indicated by arrows 374 and flow into the first collection chamber 364. From there, the red blood cells are withdrawn into the first collector 360 and flow up through the first outlet channel 322. The relatively lighter (less dense) materials follow a path indicated by arrows 378 and flow into the second collection chamber 366. From there, the less dense materials such as the supernatant are withdrawn into the second collector 362 and flow up through the second outlet channel 319.

The centrifugal device 300 includes several features that are directed to improving washing of the red blood cells. The centrifugal device 300 includes a deflector 380. Saline exiting the saline supply channel 318 passes underneath the deflector 380. In some embodiments, as illustrated, the bottom 304 of the housing 301 includes a bump out 382 to accommodate the saline supply. The deflector 380 has a periphery 384 that is sized to force the saline to flow through the red blood cell layer disposed closest to the inner surface 302 of the housing 301. As a result, the saline removes the impurities. The saline, laden with impurities, exits the centrifugal device 300 with the supernatant.

In some embodiments, blood and saline are continuously pumped into the centrifugal device 300 while the red blood cells and the supernatant are continuously pumped out of the centrifugal device 300. As a result, continuous blood salvage processing is achieved.

Figure 4:
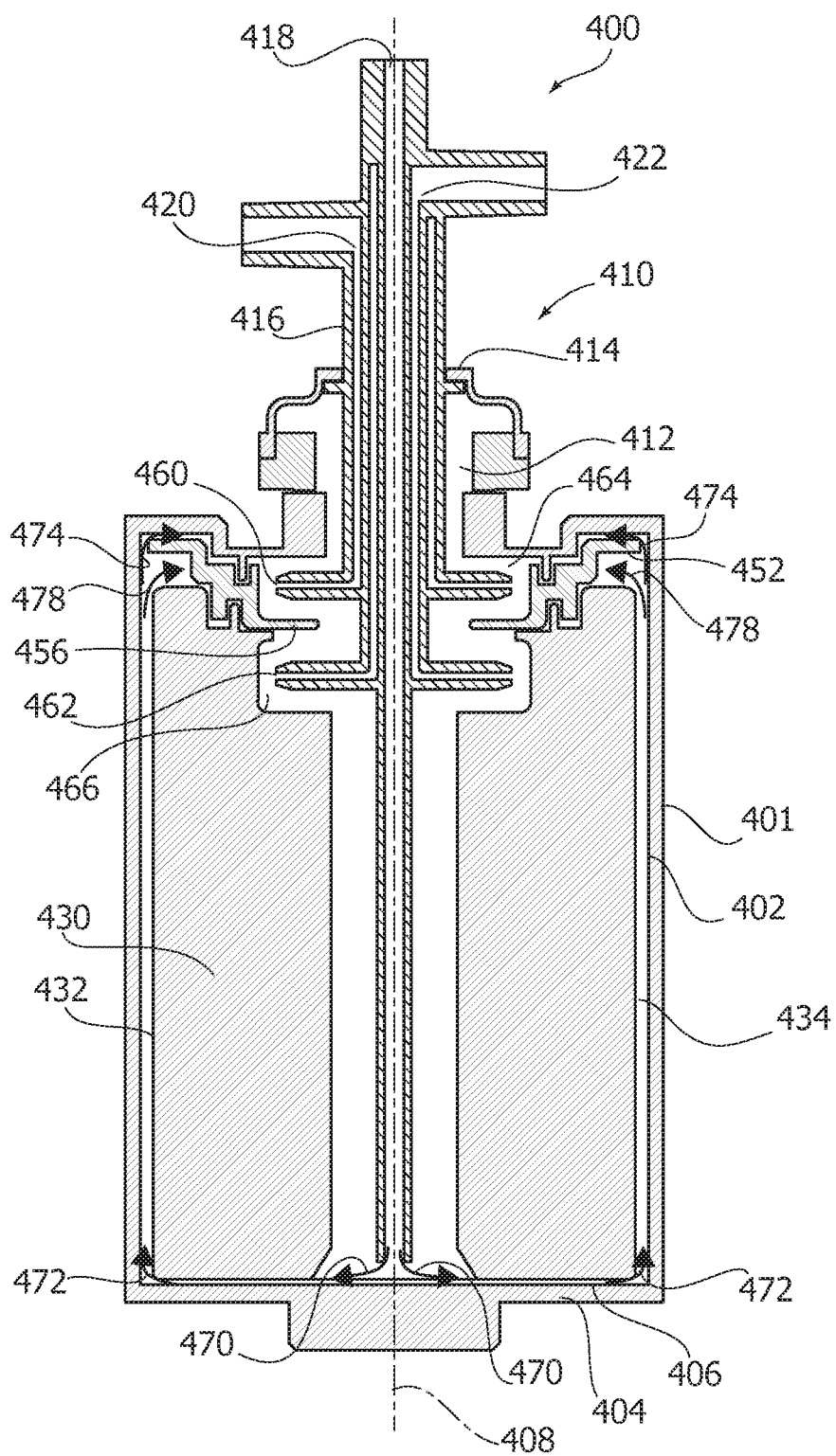
FIG. 4 is a schematic longitudinal section of the inventive continuous blood centrifugal device in accordance with an embodiment of the present invention.

FIG. 4 is a schematic illustration of a continuous blood centrifugal device 400 in accordance with embodiments of the present invention. As illustrated in FIG. 4, the centrifugal device 400 includes a cylindrical housing 401 including an inner surface 402 and a bottom 404. The bottom 404 includes an inner surface 406. The housing 401 rotates about an axis 408. The centrifugal device 400 includes an upper end 410 that has a circular opening 412 that is provided with a rotary joint 414 that forms a seal. The sealing rotary joint 414 is designed to ensure sterility inside the centrifugal device 400 and surrounds a stationary member 416 that extends into the housing 401 along the axis 408.

In some embodiments, as illustrated, the stationary member 416 includes a blood supply channel 418 for supplying blood to the centrifugal device 400. In some embodiments, the blood supply channel 418 extends downwardly (in the illustrated orientation) to a point where the blood supply channel 418 nearly touches the inner surface 406 of the bottom 404. The stationary member 416 includes a first outlet channel 420 for extracting a first separated component, such as concentrated red blood cells, and a second outlet channel 422 for extracting a second separated component, such as supernatant.

In some embodiments, the centrifugal device 400 includes a rotatable inner bowl 430 having an outer surface 432. A space 434 is defined between the outer surface 432 of the rotatable inner bowl 430 and the inner surface 402 of the housing 401. This space 434 may be sized and/or otherwise configured to permit blood components to separate within the space according to their relative densities as the centrifugal device 400 rotates. In some embodiments, the space 434 may be configured to improve or optimize the density-based separation of the blood components. In some embodiments, as illustrated, the outer surface 432 of the rotatable inner bowl 430 may have a cylindrical profile that matches the cylindrical profile of the housing 401, thereby providing the space 434 with a constant size.

In some embodiments, the centrifugal device 400 includes a barrier 450 that is disposed within the housing 401 and positioned above the rotatable inner bowl 430. The barrier 450 is concentric to the axis 408 and includes a periphery 452. A first collection chamber 464 is formed between the housing 401 and a disk portion 456 of the barrier 450. A second collection chamber 466 is formed between the disk portion 456 and the rotatable inner bowl 430. In some embodiments, as illustrated, a first collector 460 that is in fluid communication with the first outlet channel 420 is disposed within the first collection chamber 464. In some embodiments, as illustrated, a second collector 462 that is in fluid communication with the second outlet channel 422 is disposed within the second collection chamber 466.

In use, blood enters the centrifugal device 400 through the blood supply channel 418 and exits the blood supply channel 418 near the bottom 406 of the housing 401 as indicated by arrows 470. Blood passes into the space 434 as indicated by arrows 472. As blood travels upward through the space 434 as a result of centrifugal forces, the blood separates into a lighter layer relatively closer to the rotatable inner bowl 430 and a heavier layer that is relatively closer to the housing 401. The barrier 450 has an outer diameter, at least along a lower edge thereof, that spans beyond an interface (not visible) between the lighter layer (the supernatant) and the heavier layer (the red blood cells).

As a result, the relatively heavier (more dense) materials such as red blood cells follow a path indicated by arrows 474 and flow into the first collection chamber 464. From there, the red blood cells are withdrawn into the first collector 460 and flow up through the first outlet channel 420. The relatively lighter (less dense) materials follow a path indicated by arrows 478 and flow into the second collection chamber 466. From there, the less dense materials such as the supernatant are withdrawn into the second collector 462 and flow up through the second outlet channel 422.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

The invention claimed is:

1. A disposable continuous blood centrifugal device comprising:
    a rotatable housing;
    a rotatable inner bowl disposed within the rotatable housing and defining a space between the rotatable inner bowl and the rotatable housing, the space sized to permit blood to separate into layers, with a more dense layer closest to the rotatable housing and a less dense layer closest to the rotatable inner bowl;
    a first collector configured to collect blood components from within the more dense layer;
    a second collector configured to collect blood components from within the less dense layer;
    a rotatable barrier disposed within the rotatable housing above the rotatable inner bowl, the rotatable barrier configured to direct blood components within the more dense layer towards the first collector and to direct blood components within the less dense layer towards the second collector; and
    a stationary structure extending downwardly through the rotatable housing and the rotatable inner bowl, the stationary structure including a blood inlet, a first outlet in fluid communication with the first collector and a second outlet in fluid communication with the second collector, wherein the blood inlet extends to a position near a bottom of the rotatable housing, and the stationary structure further comprises a saline inlet that extends to a position near the bottom of the rotatable housing.

2. The continuous blood centrifugal device of claim 1, wherein a first collection chamber in which the first collector is disposed is formed between the rotatable barrier and a top of the rotatable housing.

3. The continuous blood centrifugal device of claim 1, wherein a second collection chamber in which the second collector is disposed is formed within the rotatable barrier or between the rotatable barrier and the rotatable inner bowl.

4. The continuous blood centrifugal device of claim 1, wherein the rotatable housing comprises a frustoconical shape.

5. The continuous blood centrifugal device of claim 4, wherein the rotatable inner bowl comprises a tapered outer surface.

6. The continuous blood centrifugal device of claim 5, wherein the tapered outer surface is configured to provide a non-uniform size of the space defined between the inner rotatable bowl and the outer housing.

7. The continuous blood centrifugal device of claim 1, wherein the rotatable housing comprises a cylindrical shape.

8. The continuous blood centrifugal device of claim 7, wherein the rotatable inner bowl comprises a cylindrical outer surface.

9. The continuous blood centrifugal device of claim 8, wherein the cylindrical outer surface is configured to provide a uniform annular shape of the space defined between the inner rotatable bowl and the outer housing.

10. The continuous blood centrifugal device of claim 1, wherein the rotatable barrier includes a disk portion that extends between the first collector and the second collector in order to reduce turbulence that could otherwise cause remixing of the blood components within the more dense layer with the blood components within the less dense layer.

11. The continuous blood centrifugal device of claim 1, wherein the bottom of the rotatable housing includes a bump out to accommodate a saline supply that is in fluid communication with the saline inlet.

12. The continuous blood centrifugal device of claim 1, further including a deflector having a periphery that is sized to force saline to flow through a red blood cell layer disposed closest to the inner surface of the rotatable housing.

13. The continuous blood centrifugal device of claim 12, wherein, when in use, saline exiting a saline supply channel passes underneath the deflector.

* * * * *